(12) United States Patent
Béguin et al.

(10) Patent No.: US 10,670,579 B2
(45) Date of Patent: Jun. 2, 2020

(54) DEVICE AND METHOD FOR SEPARATING A FLUID MIXTURE SUCH AS BLOOD

(71) Applicant: DBS SYSTEM SA, Gland (CH)

(72) Inventors: Steve Béguin, Pully (CH); Aurélien Thomas, Plan-les-Ouates (CH); Julien Déglon, Gland (CH)

(73) Assignee: DBS System SA, Gland (CH)

( * ) Notice: Subject to any disclaimer, the term of this patent is extended or adjusted under 35 U.S.C. 154(b) by 2 days.

(21) Appl. No.: 15/125,601

(22) PCT Filed: Mar. 18, 2015

(86) PCT No.: PCT/IB2015/051997
§ 371 (c)(1),
(2) Date: Sep. 13, 2016

(87) PCT Pub. No.: WO2015/140740
PCT Pub. Date: Sep. 24, 2015

(65) Prior Publication Data
US 2017/0003270 A1    Jan. 5, 2017

(30) Foreign Application Priority Data

Mar. 21, 2014   (WO) .................. PCT/IB2014/060030

(51) Int. Cl.
*G01N 33/49*       (2006.01)
*B01L 3/00*        (2006.01)
(Continued)

(52) U.S. Cl.
CPC .......... *G01N 33/491* (2013.01); *B01L 3/5023* (2013.01); *B01L 3/5027* (2013.01);
(Continued)

(58) Field of Classification Search
CPC .... G01N 33/491; G01N 33/49; G01N 33/487; G01N 33/483; G01N 33/48;
(Continued)

(56) References Cited

U.S. PATENT DOCUMENTS 5,932,100 A  *  8/1999  Yager ................ B01D 11/0492
                                                  210/511
7,282,179 B2    10/2007  Iwaki et al.
(Continued)

FOREIGN PATENT DOCUMENTS

EP       1348960       10/2003
EP       2492682       10/2003
(Continued)

OTHER PUBLICATIONS

Bannock, James H. et al, Microscale separation of immiscible liquids using a porous capillary, Anal. Methods, 2013, 5, 4991-4998. (Year: 2013).*

(Continued)

*Primary Examiner* — Christine T Mui
(74) *Attorney, Agent, or Firm* — Andre Roland S.A.; Nikolaus Schibli

(57) ABSTRACT

A lab-on-chip device for the processing, in particular the separation, of a fluid mixture comprising two immiscible phases (liquid and/or solid), said device comprising a fluid line (1,2,5,6) which successively includes an inlet reservoir (1), a separation channel (2), a collection channel (5) and an outlet (6), said separation channel (2) being designed in a way as to allow a separation of the fluid mixture into said two phases.

19 Claims, 2 Drawing Sheets

(51) Int. Cl.
*G01N 1/40* (2006.01)
*B01L 3/02* (2006.01)

(52) U.S. Cl.
CPC ..... *B01L 3/50273* (2013.01); *B01L 3/502715* (2013.01); *B01L 3/502769* (2013.01); *G01N 1/4077* (2013.01); *B01L 3/0241* (2013.01); *B01L 2200/0605* (2013.01); *B01L 2200/0631* (2013.01); *B01L 2200/0673* (2013.01); *B01L 2300/06* (2013.01); *B01L 2300/069* (2013.01); *B01L 2300/0816* (2013.01); *B01L 2300/123* (2013.01); *B01L 2300/161* (2013.01); *B01L 2400/0406* (2013.01); *B01L 2400/0481* (2013.01); *B01L 2400/0487* (2013.01); *B01L 2400/086* (2013.01); *B01L 2400/088* (2013.01); *G01N 2001/4083* (2013.01)

(58) Field of Classification Search
CPC .......... B01L 3/5023; B01L 3/502; B01L 3/50; B01L 3/00; B01L 3/5027; B01L 3/502715
USPC .......................................... 422/502, 500, 50
See application file for complete search history.

(56) References Cited

U.S. PATENT DOCUMENTS

| | | | |
|---|---|---|---|
| 7,695,629 B2* | 4/2010 | Salamitou | B01D 17/085 166/308.3 |
| 8,383,061 B2* | 2/2013 | Prakash | F16K 99/0001 422/502 |
| 9,157,903 B2 | 10/2015 | Seifried et al. | |
| 9,795,960 B2 | 10/2017 | Maillefer et al. | |
| 2002/0185184 A1 | 12/2002 | O'Connor et al. | |
| 2005/0214928 A1* | 9/2005 | Larsen | B01F 13/0059 435/287.1 |
| 2008/0073297 A1 | 3/2008 | Shiraishi et al. | |
| 2008/0248590 A1 | 10/2008 | Gulliksen et al. | |
| 2009/0107909 A1 | 4/2009 | Kotera et al. | |
| 2012/0261356 A1 | 10/2012 | Tsutsui | |

FOREIGN PATENT DOCUMENTS

| | | |
|---|---|---|
| JP | H02-016059 | 4/1990 |
| JP | 2008082896 | 4/2008 |
| WO | WO2013144743 | 10/2003 |
| WO | WO2006056787 | 6/2006 |
| WO | WO2008147382 | 12/2008 |
| WO | WO2007136057 | 10/2009 |
| WO | WO2013045695 | 4/2013 |

OTHER PUBLICATIONS

C. C. Wu, L. Z. Hong and C. T. Ou, Journal of Medical and Biological Engineering, 2012, 32, 163-168. (Year: 2012).*
Kersaudy-Kerhoas, Maiwenn, et al, Micro-scale blood plasma separation: from acoustophoreis to egg-beaters, Lab Chip, 2013, 13, 3323-3346. (Year: 2013).*
International Search Report of the priority application PCT/IB2015/051997 dated Jul. 14, 2015.
Written Opinion of the International Search Authority of the priority application PCT/IB2015/051997 dated Jul. 14, 2015.
Communication Art 94(3) EPC dated Jul. 22, 2019 from the European Patent Office for the EPO counterpart application.
Australian Patent Application 2015232998, Office Action dated Oct. 25, 2018.
Communication Art 94(3) EPC dated Mar. 9, 2018 from the European patent Office for application 15721035.2.
Communication Art 94(3) EPC dated Oct. 24, 2018 from the European patent Office for application 15721035.2.
Japanese Patent Application JP 2017-500463, office action dated Feb. 5, 2019.
Japanese Patent Application JP 2017-500463, office action dated Feb. 5, 2019 (English translation).

* cited by examiner

DEVICE AND METHOD FOR SEPARATING A FLUID MIXTURE SUCH AS BLOOD

CROSS REFERENCE TO RELATED APPLICATIONS

The present application is a U.S. national stage application of PCT/IB2015/051997 filed on Mar. 18, 2015 that designates the U.S., and claims foreign priority to International patent application PCT/IB2014/060030 filed on Mar. 21, 2014, the contents of these two documents being herewith incorporated by reference in their entirety.

FIELD OF INVENTION

The present invention relates to a device and a method which may be advantageously used for separating whole blood cells and plasma/serum, and for collecting and analyzing the generated plasma/serum, e.g. on an absorbing material. The invention is particularly suitable for dried plasma spot analysis (DPS). The plasma/serum portion of the sample, progressively generated by depletion of blood cells, can be processed (e.g. concentrated or depleted from specific proteins) and/or analyzed after separation from the blood cells enriched portion.

STATE OF THE ART

Current methods used to separate plasma from whole blood (i.e. centrifugation) generally involve several milliliters of blood. Sampling, storage, and processing of blood samples are many steps that can be improved in term of invasiveness, costs and time consumption. Today's trend in biological analysis is to reduce sampling volumes as well as reagent volumes, time, manipulation and handling of material to be analyzed. For these reasons a huge effort is conducted to develop effective point of care (POC) devices that allow on-site processing and/or analysis of biological samples.

Although biological analysis is usually performed using plasma obtained by venipuncture, the use of dried blood spots (DBS) has grown in popularity in the clinical and pharmaceutical communities over the past decade as an alternative sampling procedure. The DBS sampling process is less invasive than conventional blood sampling because only a small volume (i.e. 20 uL) is collected and spotted onto a filter paper card after a small fingerprick. Because of the ease of collection, DBS can be obtained in a non-hospital environment by minimally trained technicians or even at home by the patients themselves. In addition, most of the pathogenic agents are deactivated on the filter paper during drying (reducing the risk of infection to a minimum) whereas the analytes of interest are stable over further months at room temperature. Since blood can be maintained on a credit-card format sample at room temperature, the cost of shipping and storage of filter paper cards is substantially reduced.

The first biomedical application of DBS on filter paper dates back to 1963 when Professor Robert Guthrie introduced this alternative sampling method for detection of phenylketonuria in the newborn population. Detection of L-phenylalanine was based on a microbiological test that was sufficiently sensitive but with low analytical throughput. In the early 1990s, the development of PCR and immunoassays, including ELISA, RIA, or FIA, enabled the detection of DNA, viral RNA, antibodies, and hormones from DBS with an acceptable waiting time that was suitable for high-throughput analyses. More recently, DBS sampling form has been successfully applied to the monitoring of therapeutic agents, pharmacokinetic, and toxicokinetic studies based on liquid chromatography mass spectrometry (LC-MS). These combined advantages make the DBS procedure a patient-friendly tool for blood collection, especially in problematic and vulnerable patient populations. The ease of the process can also help in the recruitment of subjects (human and animal) for preclinical and clinical studies.

Despite of its over-mentioned advantages, DBS sampling is rarely implemented in drug development, clinical analysis nor in a broader extent to people care. Filter paper is indeed a passive support that requires external manipulations to obtain accurate volume measurement and plasma analysis. Taken together, these external steps are tedious and make the DBS not competitive enough compared to conventional venipuncture.

International patent application WO2013/144743 discloses a lab-on-chip-based system for the direct and multiple sampling, control of the volume, fluid filtration, biochemical reactions, sample transfer, and dried spot generation on the conventional and commercial cards for dried fluid spot. Within an all-in-one integrated holder, this system allows the complete process required to ensure a quantitative analysis of blood, plasma or any other fluids, modification and enrichment of molecule subsets, and formation of a dried fluid spot on the specific spot location of a passive cellulose, non-cellulose, absorbent, or non-absorbent membrane material sampling. As described for this device, plasma is obtained from a filtration process. Consequently, a filter membrane is placed in the inlet of the microfluidic channel to filtrate the fluid and separate cells from whole blood. Although of interest, this process may be not efficient enough to generate the required volume of plasma. The use of membrane may lead to the lysis of blood cells, which is not intended. In addition, the passive collection of the generated plasma into the capillary may be compromised without assistance (e.g. manual or mechanical pumping). Moreover accurate generation of a predetermined volume is delicate since the capillary is in direct contact with the membrane while it is being filled with plasma.

GENERAL DESCRIPTION OF THE INVENTION

The invention concerns a lab-on-chip device for the processing of a fluid mixture which contains at least two immiscible phases (liquid and/or solid). The device comprises a fluid line which successively includes an inlet reservoir (1), a separation channel (2), a collection channel (5) and an outlet (6), said separation channel (2) being designed in a way as to allow a separation of the fluid mixture into said two phases.

In the present text the expression "channel being designed in a way as to allow a separation of the fluid mixture into said two phases" covers a large variety of solutions which, taken as such, are already known in the prior art. The separation may be induced with specific channel dimensions, the material that constitutes the channel wall, elements located within the channel, etc . . . More generally, any technical solution that makes it possible to separate the two phases within the separation channel can be used.

The invention provides several improvements regarding the state of the art. It allows a passive separation of multiphasic fluids and suspensions (e.g. blood cells in whole blood), sample preparation, metering and isolation of processed fluid, generation of multiple dried plasma spots onto cellulose, non-cellulose, absorbent, or non-absorbent membrane material sampling without the use of a membrane or other filtration material. In addition, the volume of purified fluid (e.g. plasma/serum) which is transferred to the sampling material is controlled after its separation from raw material (e.g. blood cells and plasma/serum). It also allows the quantitative analysis of molecules on conventional dried-spots sampling cards. The device according to the invention may be used with conventional dried spot sampling supports such as #903® brand paper (Whatman, Inc., New Jersey USA), bond elut dried matrix spotting (Agilent, Germany) or treated filter papers, such as FTA and FTA Elute brand paper or DMPK A, B or C card (Whatman, Inc., New Jersey USA).

According to a preferred embodiment of the invention the microfluidic channel is sized in a way to induce sedimentation and separation of the fluidic mixture (e.g. blood cells) and generation of purified fluid (e.g. blood-cell-free plasma or serum) by capillary action.

In another embodiment of the invention the device comprises an air bubble actuator, for instance a soft push button, which, when actuated, generates an air bubble into the microfluidic separation channel in order to isolate a defined volume of processed fluid (e.g. plasma/serum). This active metering can afterwards assist the transfer of the said volume of fluid (e.g. plasma/serum) to the storage media.

In another embodiment of the invention the holding element comprises several fluid channels.

Several other embodiments of the invention are defined in the claims.

DETAILED DESCRIPTION OF THE INVENTION

The invention will be better understood below, in particular with non-limiting examples illustrated by the following figures:

NUMERICAL REFERENCES USED IN THE FIGURES

Figure 1:
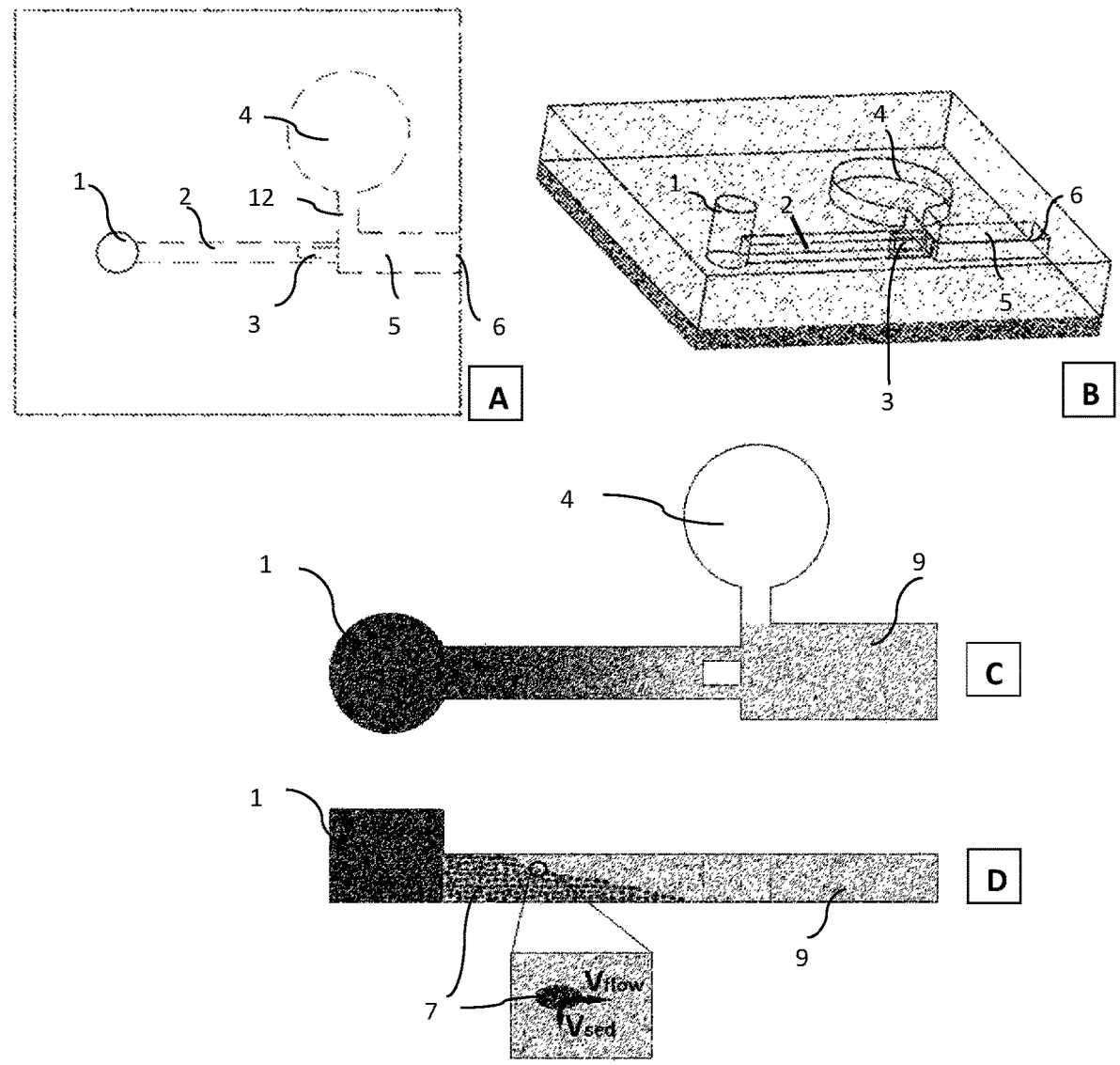
FIG. 1 shows a first example (device top view A, 3D view B, channels top view C, channels cross section D) of a device according to the invention.

1. Inlet reservoir
2. Separation (sedimentation) channel
3. Restriction element
4. Soft button
5. Collection channel
6. Outlet
7. Blood cells
8. Air bubble
9. Plasma
10. Card
11. Dried Fluid Spot
12. Metering channel
13. Outlet vertical channel In the following examples the devices are used for the separation of blood. The invention is of course not limited to such a use. Any suitable multiphasic fluid or particle suspension may be contemplated.

The device illustrated in FIG. 1 comprises a blood supply reservoir 1, a separation channel 2 (also named "sedimentation channel" in the present examples), a restriction element 3, a plasma collection channel 5, a soft push button 4 communicating with the separation channel 2 through a metering channel 12, and an outlet 6 located on the device lateral side.

A blood droplet (typically 10-50 µL) is deposited into the inlet reservoir 1. Blood cells 7 and plasma 9 are passively separated into a sedimentation channel 2 (See FIG. 1-C). The generated plasma 9 is collected in a collection channel 5. A restriction element 3, for instance a baffle, is located between the sedimentation channel 2 and the collection channel 5. The restriction element 3 ensures a proper orientation of the fluid in the direction of the collection channel 5. The geometry of the sedimentation channel 2 (length, cross section, shape, etc . . . ) has an effect on the blood dynamic within the channel 2 and thus the sedimentation properties.

Preferably, the channel geometry is chosen in a way as to induce a capillary effect, i.e. a driving force, to the fluid sample and consequently the sedimentation of blood cells before the restriction element 3 location. After the restriction element 3, the generated plasma 9 is collected into the collection channel 5 that has a determined volume. The geometry of the collection channel 5 may be adapted to modify either the plasma speed into the sedimentation channel 2 or the capillary forces that drive the fluid. As for the sedimentation channel 2, the collection channel 5 length, shape, and material are chosen in a way as to induce a capillary effect, i.e. a driving force, to the plasma 9 which is entering the channel 5.

The collection channel 5 is advantageously calibrated to receive a predetermined volume of plasma 9 (typically 1-10 µL). This volume can be modified with respect to the analysis requirements.

Figure 2:
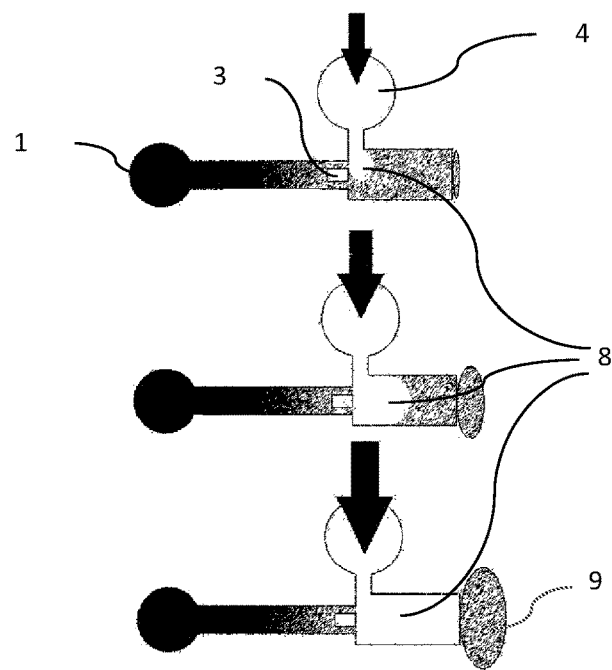
FIG. 2 demonstrates the successive formation of the air bubble to delimitate a certain volume of plasma and to assist the transfer of the said volume of plasma towards the outlet.

After the filling of the collection channel 5, a soft button 4 is manually or automatically activated by pressure or any other means. Activation of the soft button 4 induces the formation of an air bubble 8 through a metering channel 12 that ends at the entrance of the collection channel 5. The air bubble 8 sequentially allows the separation between the sedimentation channel 2 and the collection channel 5. It also allows the collection channel 5 to be mechanically emptied from the outlet 6 (see FIG. 2). Advantageously the outlet 6 may be located on the card upper side (see FIG. 3). In this case a vertical channel 13 is formed between the collection channel 5 and the outlet 6 (see FIG. 3).

Figure 4:
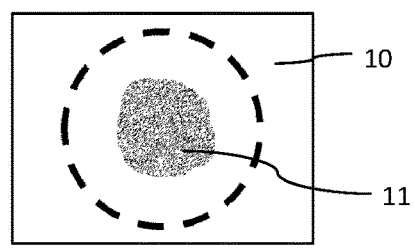
FIG. 4 shows a dry plasma spot on a storage media.

A card 10 (FIG. 4), which may incorporate cellulose and/or non-cellulose storage media, is then applied on the outlet 6 to collect the determined volume of plasma, either by directly pressing the card 10 with the fingers or by any other mean, including for instance a lid which may be clipped to the device. The contact between the card 10 and the fluid at the outlet 6 generates a dried fluid spot 11 on the card.

Figure 3:
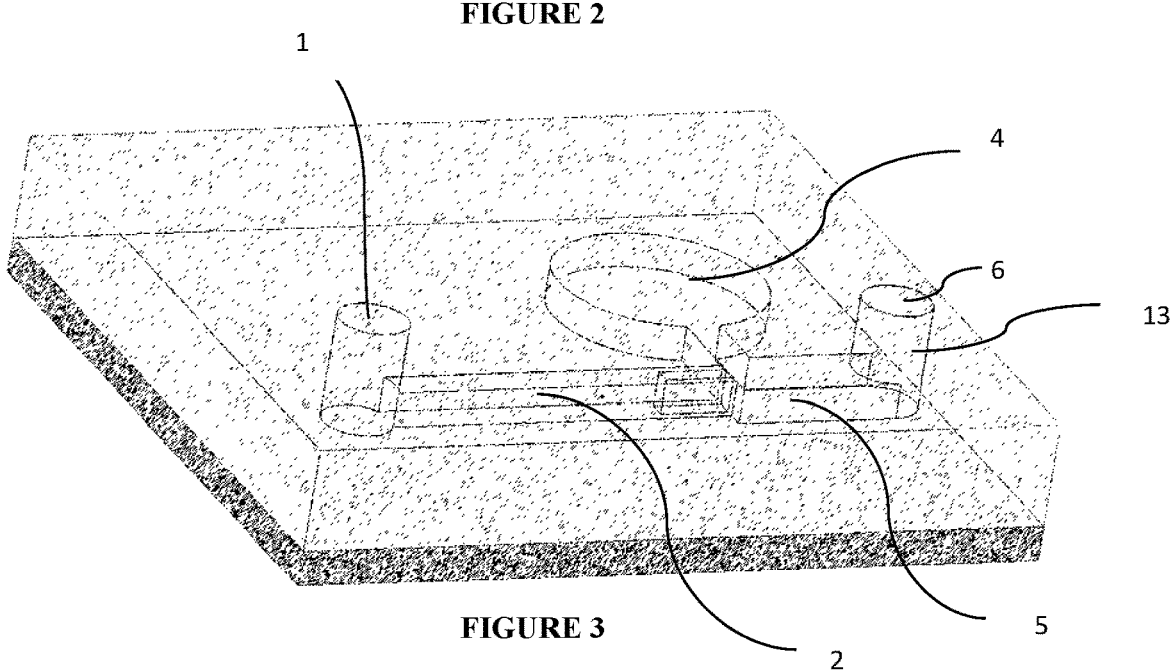
FIG. 3 shows another example (3D view) of a device according to the invention.

In the example of FIG. 3 a vertical channel 13 is defined between the collection channel 5 and the outlet 6. Advantageously, the device may contain several vertical and parallel channels (not illustrated) which are set in-line to allow multiple and independent samplings according to the number of spot locations 11 of the collection media 10. Each channel is preferably designed to produce a dried plasma spot within those spot locations 11.

The outlet 6 may have different geometries, which may be circular or non-circular.

The invention is of course not limited to the devices shown in the above examples.

The invention claimed is:

1. A lab-on-chip device for passively processing a fluid mixture having two immiscible phases, the device comprising:
   a fluid line which successively includes an inlet reservoir, an unobstructed separation channel, a collection channel, and an outlet,
   wherein the unobstructed separation channel is configured to passively separate the fluid mixture into the two immiscible phases, while keeping a liquid phase of the two immiscible phases flowing through the separation channel by capillary action,
   wherein a size of the separation channel is configured to induce sedimentation and simultaneously to provide lateral movement by the capillary action to the fluid mixture for separation of a solid phase of the two immiscible phases and simultaneous generation of a purified fluid of the liquid phase, and
   wherein the fluid mixture is blood, the liquid phase of the two immiscible phases includes at least one of blood plasma and blood serum, and the other one of the two immiscible phases includes blood cells.

2. The device according to claim 1, further comprising:
   an air bubble actuator configured to, when actuated, generate an air bubble into the fluid line to isolate a defined volume of the liquid phase.

3. The device according to claim 1, wherein dimensions of the separation channel and wettability of surfaces of the separation channel are configured to allow precise control of a filling speed.

4. The device according to claim 1, wherein dimensions of the separation channel and wettability of surfaces of the separation channel are configured to allow precise control of a shape of a front flow of the fluid mixture.

5. The device according to claim 1, wherein the collection channel directly communicates with the separation channel.

6. The device according to claim 1, wherein the collection channel is configured to include an additional fluid that is immiscible with the two immiscible phases to isolate a defined volume of the purified fluid accumulated in the collection channel.

7. The device according to claim 5, further comprising:
   an actuator for injecting an additional fluid into the collection channel.

8. The device according to claim 7, wherein the actuator is a push button formed by a thin layer of flexible material.

9. The device according to claim 5, further comprising:
   a restriction element located in the fluid line between the separation channel and the collection channel, configured to ensure an orientation of the fluid mixture in a direction of the collection channel.

10. The device according to claim 9, wherein a channel geometry of the separation channel is configured to induce the capillary action to the fluid mixture whilst providing for sedimentation of a solid phase of the two immiscible phases before a location of the restriction element.

11. The device according to claim 1, wherein the outlet is located on a lateral side of the device.

12. The device according to claim 1, wherein the outlet is located on an upper side of the device.

13. A method for using a lab-on-chip device as claimed in claim 1, the method comprising the steps of:
   filling the reservoir with a blood droplet;
   passively separating blood cells and plasma in the unobstructed separation channel;
   collecting the separated plasma in the collection channel;
   generating an air bubble at an entrance of the collection channel to separate the separation channel and the collection channel and push a fixed volume of the separated plasma towards the outlet; and
   applying a cellulose or non-cellulose sampling media onto the outlet to generate a dried plasma spot.

14. The device according to claim 1, wherein the collection channel is configured to collect the liquid phase of the fluid mixture that was separated by the separation channel.

15. A system for passively processing a fluid mixture having two immiscible phases, the system comprising:
   a chip having a fluid line which successively includes an inlet reservoir, an unobstructed separation channel, a collection channel, and an outlet,
   wherein the unobstructed separation channel is configured to passively separate the fluid mixture into the two immiscible phases while keeping a liquid phase of the two immiscible phases flowing through the separation channel by capillary action to provide the liquid phase to the collection channel, a size of the separation channel is configured to induce sedimentation and simultaneously to provide lateral movement by the capillary action to the fluid mixture for separation of a solid phase of the two immiscible phases and simultaneous generation of a purified fluid of the liquid phase, and the fluid mixture is blood, the liquid phase of the two immiscible phases includes at least one of blood plasma and blood serum, and the other one of the two immiscible phases includes blood cells; and
   a sampling media configured to be arranged at the outlet to collect the liquid phase.

16. The system according to claim 15, wherein dimensions of the separation channel and wettability of surfaces of the separation channel are configured to allow precise control of a filling speed.

17. The system according to claim 15, wherein the collection channel is configured to include an additional fluid that is immiscible with the two immiscible phases to isolate a defined volume of the purified fluid accumulated in the collection channel.

18. The device according to claim 1, wherein the passive separation of the solid phase and the liquid phase is performed without a membrane or filtration material.

19. The system according to claim 15, wherein the passive separation of the solid phase and the liquid phase is performed without a membrane or filtration material.

* * * * *